United States Patent
Sceats

(10) Patent No.: US 11,026,428 B2
(45) Date of Patent: Jun. 8, 2021

(54) BIOACTIVE MATERIAL

(71) Applicant: CALIX LTD, Pymble (AU)

(72) Inventor: Mark Sceats, Pymble (AU)

(73) Assignee: CALIX LTD, New South Wales (AU)

( * ) Notice: Subject to any disclaimer, the term of this patent is extended or adjusted under 35 U.S.C. 154(b) by 39 days.

(21) Appl. No.: 16/309,891

(22) PCT Filed: Jun. 2, 2017

(86) PCT No.: PCT/AU2017/050531
§ 371 (c)(1),
(2) Date: Dec. 13, 2018

(87) PCT Pub. No.: WO2017/219068
PCT Pub. Date: Dec. 28, 2017

(65) Prior Publication Data
US 2019/0142011 A1    May 16, 2019

(30) Foreign Application Priority Data

Jun. 20, 2016  (AU) ................. 2016902395

(51) Int. Cl.
| | |
|---|---|
| A01N 59/06 | (2006.01) |
| A61L 2/23 | (2006.01) |
| C01F 5/08 | (2006.01) |
| C01F 11/06 | (2006.01) |
| C04B 2/10 | (2006.01) |
| C04B 22/06 | (2006.01) |
| A01N 25/14 | (2006.01) |
| B01J 6/00 | (2006.01) |

(52) U.S. Cl.
CPC .......... *A01N 59/06* (2013.01); *A01N 25/14* (2013.01); *A61L 2/23* (2013.01); *C01F 5/08* (2013.01); *C01F 11/06* (2013.01); *C04B 2/10* (2013.01); *C04B 22/064* (2013.01); *B01J 6/004* (2013.01); *C01P 2004/61* (2013.01); *C01P 2004/62* (2013.01); *C01P 2006/12* (2013.01)

(58) Field of Classification Search
None
See application file for complete search history.

(56) References Cited

U.S. PATENT DOCUMENTS

| | | | |
|---|---|---|---|
| 3,920,832 A * | 11/1975 | Barer ............ | A01N 47/24 514/478 |
| 6,827,766 B2 | 12/2004 | Carnes et al. | |
| 2004/0067159 A1 | 4/2004 | Carnes et al. | |
| 2004/0266622 A1 | 12/2004 | Park | |
| 2009/0041818 A1 | 2/2009 | Otsuki et al. | |

FOREIGN PATENT DOCUMENTS

| | | | |
|---|---|---|---|
| AU | 2013904096 | 11/2013 | |
| AU | 2015904534 | 11/2015 | |
| AU | 2014339743 B2 | 1/2018 | |
| AU | 2014374829 B2 | 1/2018 | |
| WO | 2007045048 A1 | 4/2007 | |
| WO | 2007112496 A1 | 10/2007 | |
| WO | WO 2012/145802 * | 11/2012 | ............... B01J 6/00 |
| WO | 2015100468 A1 | 7/2015 | |
| WO | WO 2015/100468 * | 7/2015 | ............... B82B 3/00 |
| WO | 2016077863 A1 | 5/2016 | |
| WO | 2016112425 A1 | 7/2016 | |
| WO | 2017108760 A1 | 6/2017 | |

OTHER PUBLICATIONS

Sawei, J. et al., Antibacterial characteristics of magnesium oxide powder, World Journal of Microbiology & Biotechnology, 2000, 16:187-194.
Yin [Jin], T. et al., Antibacterial activities of magnesium oxide nanoparticles against foodborne pathogens, J. Nanopart. Res., 13, 6877-6885.
Zhou, J. et al: "Facile fabrication of mesoporous MgO microspheres and their enhanced adsorption performance for phosphate from aqueous solutions" Colloids and Surfaces: Physiochem. Eng. Aspects 379 (2011) 102-108.
International Search Report dated Jul. 31, 2017.

* cited by examiner

*Primary Examiner* — Craig D Ricci
(74) *Attorney, Agent, or Firm* — Gorman IP Law, APC

(57) ABSTRACT

A process and apparatus for manufacture of biocide products are described. The biocide properties arise from the caustic calcined powder, from carbonates such as such as magnesite and dolomite, and from hydroxides such as brucite. The method of manufacture is based on the production of high surface area oxide particles using an indirectly heated counterflow reactors for specifically calcining the carbonates and the hydroxides without significant sintering. The biocide products may be a powder or a hydrated slurry. A hydrated slurry is preferred for agricultural applications as a spray. For aquaculture applications, the products have a preferred particle size distribution to impact the aquatic and benthic ecosystems, and a Ca/Mg ratio that promotes the growth of the cultivates species when applied as a powder or a slurry. For applications such as a marine paint, the powder product or the slurry product is mixed with various agents to form a setting coating, and is applied to the infrastructure that is otherwise subject to biofilm growth.

8 Claims, 1 Drawing Sheet

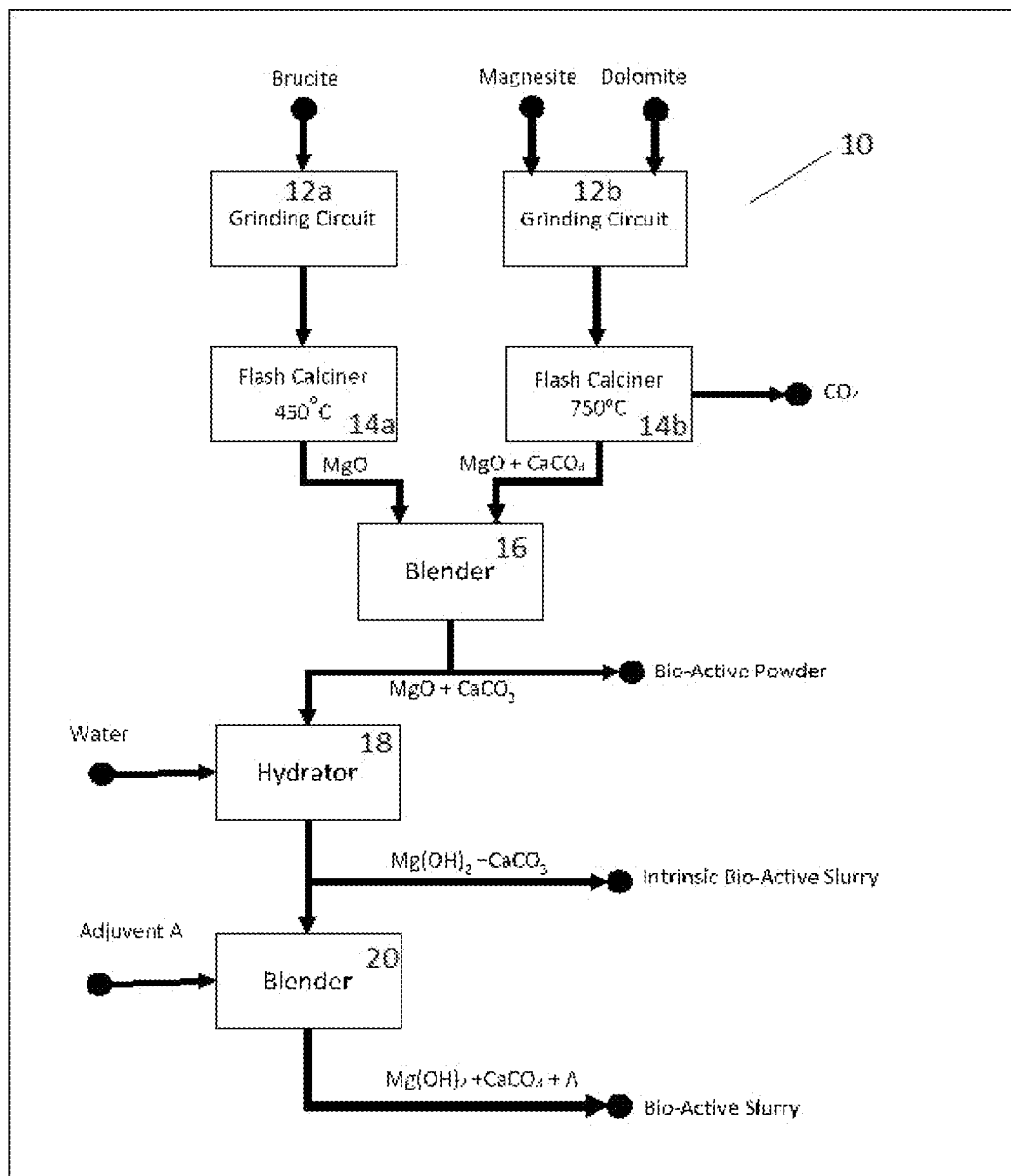

BIOACTIVE MATERIAL

This application is the National Phase Under 35 USC § 371 of PCT International Application No. PCT/AU2017/050531 filed on Jun. 2, 2017, which claims priority under 35 U.S.C. § 119 on Patent Application No. 2016902395 filed in Australia on Jun. 20, 2016, the entire contents of each of which are hereby incorporated by reference.

TECHNICAL FIELD

The present invention relates broadly to the production of a material product that is a contact biocide for use in agriculture, aquaculture and other applications, and which is produced from calcined powders using flash calcination of materials. This invention is a further development of a generic bioactive material, and its method of manufacture, described by Sceats (A U2014374829) and Sceats and Hodgson (A U2015904534), included herein in their entireties, in which the general method of manufacture described therein is further adapted for the production of material by optimising the bio-activity, by extending the range of the materials that can be used to manufacture the product, and thereby extending the range of applications of the product.

BACKGROUND

Sceats, and Sceats and Hodgson, focused on the application of the product to agriculture, but there is a broader range of potential applications. For example, in 2016, aquaculture farming production, especially for fish, molluscs and crustaceans, exceeded that from wild capture commercial fishing. This transition has been driven by demand from growing human populations and the stagnation of wild capture. The Food and Agriculture Organisation (FAO) of the United Nations has reported that in 2015 the world aquaculture production reached 97.2 million tonnes (live weight) with an estimated value of USD157 billion in 2013 with a growth rate of 5.6%. The FAO reports that its Global Aquaculture Production statistics database shows that 575 aquatic species grown in freshwater, seawater and brackish water have been registered.

Intensive aquaculture farming practices are rapidly evolving, compared to those of agriculture, which have evolved over thousands of years. The very high population density of the cultivated species in farming compared to the wild leads to the occurrence, severity and spread of diseases within and between aquaculture populations in ways that are similar to those associated with diseases in dense human and terrestrial animal populations. Factors that impact on the development and severity of a disease following exposure of the cultivated species to a pathogen include the virulence of the pathogen, the immune, genetic and physiological condition of the cultivated species; and its stress and population density; as well as the general environmental conditions of both the aquatic and benthic ecosystems of an aquaculture pond or pen. The cultivated species population density is the most important factor in the spread of diseases in aquaculture, because of the increased rate of infection. This dense population in the aquatic environment, and the limited water flow, facilitates the spread of pathogens, and the benthic environment is often a source of such pathogens. The development of a disease and the relevant severity of that disease within the cultivated species population is influenced by a complex interaction of these variables associated with the pathogen, the cultivated species and these two environments.

There is a third ecosystem in aquaculture systems, which is the pond or pen infrastructure that may comprise the wall structure of the pens, the bottom of boats, and equipment used to manage the farm such as feeders and boats. These surfaces are subject to the growth of biofilms, and the impact of these films on this critical infrastructure has a significant economic impact. Biofilm growth suppression had previously been prevented by the use of very toxic materials, such as tri-butyl tin. However, this material leached the toxic materials into the aqueous ecosystems, and many such compounds have been subsequently banned in most countries. Other systemic biocides have been deployed that have a reduced impact, but there are concerns about the potential for such systems to leach, as well as the growth of resistance. There is a need for a non-toxic coating material of marine infrastructure such as wharves, piles, nets, ships and boats that can suppress the growth of biofilms, and in the context of aquaculture, this includes all the surfaces of the aquaculture pens and systems. The ability of pathogens to move between the aquatic ecosystem, the benthic ecosystem and this infrastructure ecosystem means that all three ecosystems need to be managed in aquaculture.

The ecosystems in aquaculture comprise the aquatic, benthic and infrastructure zones. The pathogen are may first incubate in the benthic zone and then progress to the aquatic zone, because the benthic zone often becomes polluted more quickly. In addition, systemic biocides are often applied to the aquaculture systems just to prevent biofilm generation, and these can find their way into the aquatic and benthic ecosystems. Therefore, aquaculture is therefore difficult to target with systemic biocides. There is a search for materials that can mitigate the development and spread of diseases so that costly intervention with systemic biocides is rarely required and prudently applied. Such a material would likely be a contact biocide to ensure that it is active against a wide spectrum of diseases.

Just as for agriculture, there is a need for methods of infectious disease controls that preferably impacts positively against the pathogen, while benefiting the cultivated species and the environment. However, the same sets of issues arise in aquaculture as in agriculture and human health, whereby diseases in the cultivated species rapidly become tolerant to systemic biocides through adaptation. Such biocides are generally neurotoxic compounds, which are toxic to both humans and animals. In aquaculture, the use of such compounds is limited because the cost of chemicals generally exceeds the benefits. For a contact biocide application in aquaculture, the contact requirement is met by a material that is largely insoluble, and an additional challenge would then be to find a means of application in which contact can be made in each of the aquatic, benthic and infrastructure ecosystems.

There has been an extensive development of nano-materials with biocide properties, and in particular, of nano-magnesia MgO and nano-zinc oxide ZnO. An example of a biocide is 'Antibacterial characteristics of magnesium oxide powder', J. Sawei et. al. World Journal of Microbiology and Biotechnology, 16, Issue 2, pp 187-194 (2000) and T. Y in and Y. He, 'Antibacterial activities of magnesium oxide nanoparticles against foodborne pathogens' J. Nanopart. Res. 13, 6877-6885. In the study by Sawai et al, the objective was to make high surface area MgO with particle sizes below about 50 nm. In trials of these materials, the MgO particles rapidly react with water to form nano-magnesium hydroxide $Mg(OH)_2$. Prior art references to nano-MgO are ascribed herein to nano-$Mg(OH)_2$. These hydrated nano-materials exhibit broad spectrum bioactivity response to viruses, bacteria and fungi. However, the cost of production of nano-materials is such that they are rarely deployed in aquaculture. Furthermore, there are concerns about the toxicity of nanomaterials in general because they are readily entrained in breaths of air, and fast diffusion through the skin.

The process for production development of nano-active $Mg(OH)_2$ from carbonate minerals such magnesite and dolomite has been described, for example, by Sceats and Sceats and Hodgson. In that approach, $Mg(OH)_2$ particles in the range of about 0.4-100 microns are produced which are composites of nano-scale crystallites in an aqueous solution. Tests of the effectiveness in agriculture have demonstrated that these materials have the same bio-active responses to bacteria, fungi and viruses as the $Mg(OH)_2$ nano-particles, and they are therefore deemed to be nano-active. The larger particles are in an aqueous solution, and are not entrained in air for breathing, and the particles are too large to diffuse through the pores in the skin. The toxicity to humans is the same as large $Mg(OH)_2$ particles, as in Milk of Magnesia, but the material retains the nano-activity to pathogens through their nano-crystalline structure. In this invention, that approach to production is extended to the use of brucite as a source of MgO, with the brucite being either a mineral or a synthetic material produced from brine.

In agricultural applications, the bio-activity is generally realised by diluting the slurry in water, and applying it to leaves of plants as a foliar spray. Without being bound by theory, the bio-activity observed in agricultural tests as a spray is ascribed to the release of Reactive Oxygen Species, such as peroxide and superoxide radicals that are produced on the high energy edges of the MgO nano-crystallites that are formed during flash calcination of Magnesium Carbonate, for example in the calciner described by Sceats and Horely (PCT Patent Application No. WO2007045048) and included herein in its entirety. These chemical species survive hydration, for example, in the process described by Sceats and Vincent (A U 2014339743) and included herein in its entirety, to make a stable magnesium hydroxide slurry, with up to 60% of the active ingredient as $Mg(OH)_2$. It has been observed that the particles adhere to the plant leaf, and the particles gradually degrade as the magnesium is ingested through the leaves as a fertiliser, to assist the production of chlorophyll. It is believed that, in this prior art, the bio-activity is achieved through the gradual release of ROS, which prevents the leaf ecosystem from becoming anaerobic, and thereby preventing disease. A common feature of many diseases is that the pathogens initially grow in anaerobic conditions. In that sense, the nano-active materials are disease preventative contact biocides, and the diseases do not develop immunity. The concentration of ROS is generally not sufficiently high that it has an adverse impact on aerobic bio-organisms. Specifically, the ROS and the alkali, $Mg(OH)_2$, in the particles both promote an oxygenated ecosystem, and in such systems pathogenic microbes do not thrive. No substantial persistent bioactivity has been observed in $Mg(OH)_2$ produced from MgO produced from conventional calciners, and this loss is attributed to the sintering of the nano-crystalline surfaces, which is correlated with the recombination of the ROS species with the trapped electrons.

In aquaculture, the cultivated species are animals that are generally very sensitive to stress, and are intolerant to toxic chemicals that might be tolerated by plants. Therefore, the broad spectrum toxic disease preventatives that are used in agriculture for plants generally cannot be used in aquaculture. Most generally, products that are toxic to humans are also toxic to animals such fish and shellfish. Moreover, the use of drugs developed as disease preventatives for humans, such as antibiotics, show the same evolution as observed in humans, namely the loss of bio-activity overtime as the diseases develop strains that are resistant to the drugs. There is a need in aquaculture for disease preventative products that are non-toxic to the cultivated species and to humans, and which are broad based in their activity so that the pathogens do not become resistant to the use of the product.

In aquaculture, the cultivated species are fish, molluscs and crustaceans. The primary method of disease prevention in the cultivated species has been to use successful treatments from land based animal husbandry. In aquaculture, the most common treatments involve adding bioactive materials to food that is fed to the cultivated species and ingested. These treatments often use systemic drugs. However, the quantity of bioactive materials required to achieve disease prevention are very large, and the costs are very high. The poor performance is a result of the aqueous environment. Soluble compounds may dissolve in the water before the cultivated species eat the food, and there are large losses of the bioactive materials. Furthermore, such compounds are taken up by all the species in the water, from plants, plankton, other aquatic animals, as well as the cultivated species. If compounds are stabilised in particles, any uneaten particles fall to the bottom of the pond, then the bioactive materials are taken up by the benthic ecosystem on the pen or pond floor. These practices are generally deemed to be unstainable, and the resistance to diseases in all the biota has the propensity for significant undesirable long term effects in the whole ecosystems. There is a need fora non-toxic disease preventive that is non-toxic to the cultivated species, but is also beneficial to the environment of the pond, and specifically to the long term healthy ecosystem of the water. Most generally, there is a need for a product for aquaculture that is a disease preventive that has no toxicity impact on the cultivated species or the other animal species that inhabit a healthy aquaculture system, including both the aqueous, the benthic and infrastructure ecosystems. The nature of the ecosystems in aquaculture vary significantly throughout the world because they are dictated by the cultivated species natural habitat and farming practices. The ability to prevent disease depends on maintaining healthy aquatic, benthic and infrastructure ecosystems.

For example, a particular problem arises in aquaculture ponds that are constructed from, or located near, acid-sulphate soils. Such soils are often found in areas surrounding mangrove swamps. In mangroves, the conditions are anaerobic and reducing, and iron is deposited as pyrites (ferrous sulphide), which accumulate and persist over geological timescales. When aquaculture ponds are produced from such soils, or the soils are disturbed, for example, from water run-off and flooding, the pyrites is released into the water and in such oxidising conditions, the pyrites is sequentially oxidised, firstly releasing ferrous and sulphide ions, followed by further oxidation to ferric ions and sulphuric acid, such that the pH falls, releasing aluminum ions into solution. The iron and aluminum ions are toxic to species such as prawns, resulting in significant kills of cultivated species. Eventually, the ions are removed through the formation of insoluble iron oxide particles, which are fall into the sludge. On a long timescale, the reducing conditions in the mud form pyrites, and the cycle will continue when the mud is disturbed and exposed to oxygen. There is a need for a material that can be added to the water in a new aquaculture pond, or a pond that has been disturbed by flooding, that not only prevents pathological disease from microbes for such cultivated species, but which also rapidly removes the toxic iron and aluminum ions from solution.

The heavy metals, such as cadmium, copper, lead, chromium, arsenic, barium, cobalt, manganese and vanadium are toxic to most cultivated species in aquaculture. The bigger problem is that these metals may be concentrated by accumulation, such as in the gills of fish, through the use of recirculated water, or by natural events (floods and the like). The major issue is generally not the toxic effects on the cultivated species because the concentrations are normally low, but the health impact on humans arising from the accumulated levels of heavy metals in the human body over a long time from eating such cultivated species. There is a need for a material that can remove heavy metal ions from aquaculture ponds.

A more general issue arises from the water contamination from excretions which cannot disperse because of the dense population, the high food consumption, and low water flow. Of particular concern is the high concentrations of phosphorous, as phosphate ion, and nitrogen, as urea and ammonia. These may cause eutrophication and hypoxia, in the pond or in downstream water. Increasingly, aquaculture farmers are under pressure to reduce the leakage of these materials from aquaculture pens and ponds. There is a need to remove phosphorous, as phosphate, and nitrogen, generally as ammonia, from aquaculture pens and ponds on the basis that excess amounts of these cause stress on the cultivated species, but also adversely impact on the environment in and around the aquaculture ponds. There is need to remove excess phosphorous and nitrogen from the water in aquaculture pens.

The prior art of Sceats, and Sceats and Hodgson, cited above, discloses the production and use of nano-active materials from carbonate compounds to produce a biocide for application in agriculture and aquaculture, and other applications such as protection of food to infestation of microbes that induce diseases in humans. The carbonate precursor identified in that patent is the mineral magnesite, $MgCO_3$. Magnesite is a relatively rare mineral, and is usually characterised by a significant amounts of impurities including sand, dolomite, talc and clay. Beneficiating the mineral to achieve high purity mineral feedstock is costly. There is a need to extend the range of precursors that can be used to produce nano-active $Mg(OH)_2$.

Any discussion of the prior art throughout the specification should in no way be considered as an admission that such prior art is widely known or forms part of common general knowledge in the field.

SUMMARY

Problems to be Solved

It is an object of the present invention to provide a process to optimise the product for the specific use in aquaculture, where the product is to be bio-active in both the aquatic and benthic ecosystems, and to be a non-toxic food additive for ingestion by the cultured species.

It is an alternative object of the present invention to provide a process to manufacture a product or a product for the restoration the aqueous ecosystem in aquaculture which may be adversely impacted by heavy metals, by eutrophication from phosphorous and nitrogen, and excess turbidity from solid particulates such as clays and iron oxide.

It is another alternative object of the present invention to provide a process to manufacture a product or a product for the restoration of the benthic ecosystem in aquaculture which may be adversely impacted by septic conditions.

It is yet another alternative object of the present invention to provide The prior art of Sceats and Hodgson claimed the application in aquaculture, and subsequent tests demonstrated that the performance may be enhanced by more specific specifications, now claimed in this invention.

It is an alternative object of the present invention to reduce the adverse impact of biofilms on the infrastructure of the aquaculture pond or pen, and more generally for all marine infrastructure, such as ships, boats, buoys, and wharves.

Means for Solving the Problem

A first aspect of the present invention provides a process for producing a biocide powder, comprising the steps of:
  Selecting one or more carbonate compounds with a predetermined calcium/magnesium ratio;
  Grinding the carbonate compounds to produce a carbonate powder with a first predetermined particle size distribution;
  Selecting a magnesium hydroxide compound;
  Grinding the hydroxide compound to produce a hydroxide powder with a second particle size distribution;
  Calcining the carbonate powder in an externally heated counterflow flash calciner at a first temperature to produce a calcined mixture having a surface area sufficiently high enough to exhibit bioactivity;
  Calcining the hydroxide powder in an externally heated counterflow flash calciner at a second temperature to produce a calcined oxide with a surface area sufficiently high enough to exhibit bioactivity; and
  Blending the calcined mixture and the calcined oxide in a predetermined proportions.

Preferably, the process further comprises the step of adding ground limestone, or lime or hydrated lime to the form the biocide powder.

Preferably, the carbonate compounds comprising Magnesite and Dolomite.

Preferably, the degree of calcination of the magnesium carbonate in the magnesite and dolomite is in the vicinity of 95% or more, and the degree of calcination of the calcium carbonate is in the vicinity of 5% or less.

Preferably, wherein the calcined mixture and calcined oxide comprises magnesium oxide (MgO).

Preferably, the surface area of the magnesium oxide is ranged from 200 m2/gm to 300 m2/gm.

Preferably, the magnesium hydroxide compound comprises mineral brucite or magnesium hydroxide powder produced from seawater or brine in which the degree of calcination of the magnesium hydroxide is around 95% or more.

Preferably, the surface area of the oxide from the hydroxide powder is above 200 $m^2$/gm of MgO, and preferably above 250 $m^2$/gm of MgO and most preferably above 300 $m^2$/gm of MgO.

Preferably, the particle size distribution of the ground carbonate compounds is in the range of about 1 to 100 microns, with the particle fraction in the range of 1 to 10 microns.

Preferably, the particle size distribution of the ground magnesium hydroxide compound is in the range of about 1 to 100 microns with the distribution in the range of 1 to 10 microns.

Preferably, the particle size of the ground limestone or lime is in the range of about 1 to 100 microns.

Preferably, the blend of the powder produced from carbonate; the powder produced from hydroxide depends on the availability of the carbonate and hydroxide input materials and the specification to achieve a predetermined Ca/Mg ratio.

Preferably, the proportion of limestone, lime or hydrated lime depends on the specification to achieve a desirable Ca/Mg ratio for the application and to achieve a desirable viscosity and stability of the slurry in conjunction with the amount of carboxylic acid added in the slurry production process.

Preferably, the first temperature is different to the second temperature.

Preferably, the first temperature is about 750° C.

Preferably, the second temperature is about 450° C.

Preferably, the process further comprises the step of:

Hydrating the biocide powder with water at or near the boiling point of water until the hydration is completed;

Applying a shear mixing, and

Adding a carboxylic acid or salt as the thinning agent, in order to form a stable, readily thinned, slurry of the hydrated oxide with about 60% solids in the final product.

Preferably, the process further comprises the step of quenching the slurry to below 60° C.

Preferably, the process further comprises the step of cooling the slurry to ambient.

Preferably, the process further comprises the step of adding additives to the slurry Preferably, the additive is an aqueous solution of hydrogen peroxide.

Preferably, the additive is ozone, which is sparged into the slurry.

Preferably, the biocide powder is adapted to use in agriculture, food, water treatment, chemical detoxifier, and industrial applications such as rubber production, the Ca/Mg ratio being around 5% to less than 2%.

Preferably, the biocide powder is adapted to use in aquaculture, the Ca/Mg ratio being around more than 5% to 15%.

Preferably, the biocide powder is adapted for an application as a biocide spray, a foam or a fog wherein the slurry or powder is mixed with oil to form an emulsion if required, and processed into a foam or fog.

Preferably, the biocide powder or slurry product for application as a biocide paint, including a marine paint to prevent biofilm growth wherein the slurry of powder is mixed as a filler into a paint formulation that may be either water or oil based.

Preferably, the carboxylic acid is acetic acid, and the carboxylic salt is magnesium or calcium acetate.

In another aspect of the present invention, there is provided a reaction apparatus for producing biocide powder or a chemical detoxifier powder or a catalyst support from a carbonate mineral, comprising:

a grinder for carbonate compounds a grinder for hydroxide compounds an externally heated counter flow flash calciner that produces high surface area oxides from the ground carbonate;

an externally heated counter flow flash calciner that produces high surface area oxides from the ground carbonate; and a blender in which the calcined solid powders are mixed together, and or with other ground solids for the production of a biocide powder.

Preferably, the reaction apparatus further comprises hydration reaction vessel for the production of the slurry product having an inlet for the blended powder and a water inlet; and a shearing apparatus for shearing the reaction mixture; and a steam outlet for release of steam from the reaction vessel, such that in use the reaction is controlled by allowing heat of hydration to raise the temperature of the reaction mixture, allowing water to boil off from the reaction mixture as hydration proceeds, and removing steam via the steam outlet to remove excess heat and control reaction temperature at boiling point; and a means of quenching the slurry to below 60° C., preferably by transfer of the slurry to a cooled container and a means of cooling the slurry to ambient temperature; and a means of adding solid or liquid additives to the slurry.

Preferably, the reaction apparatus for post-processing the bioactive power or slurry from the apparatus by one or more of the following steps:

sparging the powder or slurry with a gas adjuvant such as ozone to enhance bioactivity; or adding and mixing liquid adjuvant compounds to the powder or slurry to enhance bioactivity; or adding and mixing materials to the powder or slurry to make a biocidal coating product or adding and mixing materials to the powder or slurry to make a biocidal emulsion or foam.

In another aspect of the present invention, there is provided a chemical composition as a powder adapted for use as a biocide, wherein the composition comprises: a powder of micron scale calcined particles which are formed from a mixture of carbonate compounds and hydroxide compounds, and which have additives to boost the biocide impact such as ozone, hydrogen peroxide wherein the particles have a porosity of greater than 0.5 and wherein the pore surface is largely composed of nano-crystalline structures.

Preferably, the chemical composition is presented as a slurry adapted for use as a biocide, wherein the composition comprises a slurry produced by hydrating the powder with additives that stablise the slurry.

Preferably, the chemical composition is presented as a coating material slurry adapted for use as a biocide, wherein the composition comprises a coating material produced by mixing the powder or the slurry with additives that set the material when applied to a surface.

Prefer the chemical composition is presented as a foam, spray or emulsion material slurry adapted for use as a biocide, wherein the composition comprises a foam, spray or emulsion material produced by mixing the powder or the slurry with additives that form a foam, spray or emulsion when processed.

In the context of the present invention, the words 'comprise', 'comprising' and the like are to be construed in their inclusive, as opposed to their exclusive, sense, that is in the sense of 'including, but not limited to'.

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

BRIEF DESCRIPTION OF THE FIGURES

FIG. 1 depicts a schematic drawing of a process for production of a powder or a slurry from powders of mineral magnesite, dolomite or brucite in which the powder particle size, porosity and surface area are optimised by calcination to form a biocide.

DESCRIPTION OF THE INVENTION

Preferred embodiments of the invention will now be described with reference to the accompanying drawings and non-limiting examples.

FIG. 1 depicts a schematic drawing of a process for production of a powder or a slurry from powders of mineral magnesite, dolomite or brucite in which the powder particle size, porosity and surface area are optimised by calcination to form a biocide.

One example form of manufacture of the product which can be described by consideration of the process flow of FIG. 1 for the mineral precursors of magnesite and dolomite as carbonate compounds and brucite as a hydroxide compound. Other minerals particulate impurities in a mined mineral may include sand, talcs, and clays. The desired material product is either a bioactive powder or a bioactive slurry. The desired solid product may be made solely from the carbonate materials, or the hydroxide materials, or a combination of either, and a by-product from the carbonate compound processing may be a pure carbon dioxide gas.

The hydroxide compound may be a mineral brucite or a synthetic brucite for example, produced from sea water or brines in the known art by precipitating the hydroxide from sea water or brines by the addition of limestone. The synthetic material is called herein brucite, although it may have a different crystalline structure from the mineral.

In this embodiment, the 10 comprises the following steps:

Grinding the feedstocks (steps 12*a*, 12*b*);

Calcining the ground materials (steps 14*a*, 14*b*);

Blending the calcined materials (steps 16);

In another embodiment, the process 10 may comprise a further step of adding ground limestone, or lime or hydrated lime to the form the biocide powder.

In yet another embodiment, the process 10 may comprise a further step of hydrating the blended powder to form a slurry product (step 18).

In yet another embodiment, the process 10 may further comprise a step of enhancing the bioactivity of the slurry with adjuvants as an option (step 20).

In one embodiment of the present invention, the first step of process 10 is one in which the desired particle size distribution is achieved by crushing and grinding the compounds (steps 12*a*, 12*b*). The magnesite and brucite are the primary sources of nano-active $Mg(OH)_2$ in the final product, whereas the dolomite is the primary source of calcium. These minerals may be found within a mine site and are selectively mined, or in the case of brucite, synthesised. In this embodiment the hydroxide compound are ground separately from the carbonate compound. It is known in the art that the brucite grinds very differently to the other minerals by virtue of its different crystal structure, which is such that the mineral rapidly flakes to during grinding give small particles in the range of 0.4-15 microns. In this embodiment, the process for production of brucite is taken to be unchanged from that used to make, for example, brucite for the manufacture of refractories, in which the process is optimised to facilitate ease of filtering, drying and compacting for subsequent calcination in a kiln. That is, the particle size distribution exceeds the preferred distribution of say 0.4-100 microns. In this embodiment, the dried particles are ground. This may preferably be done by first sieving the particles to remove the fraction above 100 microns, and then grinding the oversized fraction to produce particle with sizes in the range of 0.4-15 microns. A number of sieving and grinding stages can be performed to give the desired particle size distribution for the application.

In this embodiment, the desired particle size distribution of the ground carbonate compound may be achieved in a number of grinding stages, followed by mixing. For example, a single grinding process may not provide a sufficient number density of small particles, such that a fraction of the coarsely ground material may be finely ground, and remixed with the residual coarsely ground fraction. The art of obtaining a desired particle size distribution by such comminution processes is a known art per se. The desired particle size distribution is typically in the range of 0.4-100 microns.

In this embodiment, the fraction of dolomite in the ground material is set to give the desired calcium/magnesium ratio for the desired application. For example, in aquaculture, For aquaculture, a typical desirable Mg/Ca ratio on a molar basis is in the range of about 6:1-4:1. While it is possible to use ground limestone as the source of the calcium, the availability of the calcium carbonate from limestone is lower than that which is available from the calcined dolomite, described below, by virtue of the higher porosity and surface area of the calcined dolomite compared to ground limestone.

The second step of the sample embodiment is calcination. The ground carbonate compound is processed by calcination, as described by Sceats and Hodgson to create the nano-scale crystallites that are believed to be the source of the bioactivity. This step of the process is that of calcination of the carbonate in which the $MgCO_3$ in the magnesite and dolomite is calcined. It is important that the processed particles exhibit minimal sintering during the calcination process, and achieve a degree of calcination of the $MgCO_3$ sites, in the magnesite and dolomite, that is preferably in excess of 95%. The most fundamental measure of the deleterious impact of sintering is the specific surface area. The experimental results show that the calcination of the dolomite MgO site does not generate nano-scale crystallites of MgO with super-oxide formation to create a biocide. Without being limited by theory, it is reasonable to assume that the uncalcined $CaCO_3$ moeities in the dolomite prevents the formation of MgO nano-crystallites because there is insufficient time during flash calcination for diffusion and aggregation of nano-structured MgO to occur, as reasoned by Sceats and Horley in AU 2006904553. Extending the time leads to sintering and phase separation with no nano-scale crystallites. The surface area that provides the bioactivity of the calcined product is that of the MgO from magnesite alone. This can be deduced from surface area and calcination measurement, and should be 200 $m^2$/gm of MgO from magnesite, and preferably greater than 250 $m^2$/gm of MgO and more preferably greater than 300 $m^2$/gm of MgO. The type of calciner is critical to achieving the properties described above. The basic requirement is that the process is very fast to eliminate the effect of sintering, and this should be preferably several seconds. This means that the process is flash calcination. The second requirement is that the particles experience the lowest possible temperature during this time. Conventional flash calciners drop the particles into a very hot combustion gas, and from that time, the temperature of the gas decreases as the reaction extract energy from the gas stream. Further, not all particles experience the same conditions. The net result is that the outer surfaces of the particles are extensively sintered, and it is difficult to achieve surface areas in excess of 50 $m^2$/gm of MgO. The small particles are most extensively sintered. The preferred calciner is that described by Sceats and Horely, for example in WO2007/112496 (incorporated herein by reference). In this case, the temperature of the particles flowing through the calciner steadily increases for all particles, and the maximum temperature they experience is the exhaust temperature. During the calcination, there is generally some decrepitation of the input particles, and often a shoulder appears on the particle size distribution in the region of 0.1-1 microns. Control of the external burners along the calciner provides the desired heat transfer to the particles, and the degree of calcination and surface area can be controlled. This system is known per se, and is capable of operating at production levels of about 5 tonnes per hour for particles that are 95% calcined for the Mg site, with a surface area of greater than 200 $m^2/gm$ of MgO from magnesite. The important factor which determines the biocidal impact is the high surface area of the MgO from the magnesite in the calcined powder. For the calcination of magnesite and dolomite the exhaust temperature from the calciner is preferably about 750° C., at which temperature about 95% calcination of the MgCO3 is achieved, less than about 3% calcination of the $CaCO_3$ is achieved.

The calcination process for the ground hydroxide compound is similar to that described above for the ground carbonate compounds, except that the temperature of the exhaust of the calciner is preferably lower than about 450° C., at which temperature 95% calcination of the $Mg(OH)_2$ to nano-active MgO is achieved with a surface area greater than 120 $m^2/gm$ of MgO. This process has not previously be described. Generally, multiple hearth furnaces can produce MgO from magnesium hydroxide with a surface area of typically 50-100 $m^2/gm$, and such MgO does not display the required nano-active properties required for biocidal activity. At higher exhaust temperatures of above about 450° C., for a given calciner, the sintering of the particles dramatically reduces the surface area.

It highly desirable that the calciner design, of the type, for example, described by Sceats and Horely, is its capability for processing either the hydroxide compound at about 450° C. or the carbonate compound at about 760° C. That is, in the embodiment of FIG. 1, the two calciners shown can mean the same equipment operating under different settings at different times.

The third stage of the embodiment of FIG. 1 shows that the powder streams from the two calcination processes being mixed to form the biocide powder product. This product has the desired particle size distribution and the Ca/Mg ratio to suit the application. This powder is a biocide, and can be used in application where a powder form is used, either directly or indirectly as a feed for the manufacture of products such as coatings.

Where a slurry product is desirable, the fourth stage of the process is to hydrate the slurry. This process is well described by Sceats and Vincent for example in AU 2013904096 (incorporated herein by reference), as a process that can produce tonnes of slurry per hour to match the production rate of the calciner described above. The high surface area of the particles is such that the hydration reaction, when mixed vigorously, liberates a large amount of heat and boils the water. This establishes a set point and the thermally activated hydration occurs at the boiling point, and the excess heat is liberated by boiling. The application of a shear mixer provides the agitation required for a uniform controlled process. During the course of the reaction, acetic acid is added to the slurry to provide thinning necessary for the shear mixer to operate. The reaction is complete when the temperature starts to drop from the heat losses. It is preferred to quench the slurry quickly below 60° C., and then let the slurry cool to ambient for the next processing step. The net result is a slurry that has hydrated, and which is stable over many months with regard to sedimentation, and which is readily shear thinned to allow pouring and processing. This slurry has the same intrinsic biocide activity as has nano-particles when diluted in water for application as a foliar spray. Importantly, there is no significant loss of biocide activity during over the slurry lifetime of several months.

The fifth stage is the option, if required, to add adjuvants to either the powder or the intrinsic slurry product described in order to increase the biocide properties above that of the intrinsic biocide response considered below. There are many such adjuvants. Examples are hydrogen peroxide, or ozone, which can be added to saturate the crystalline binding sites on the $Mg(OH)_2$ surfaces with the radical species being the superoxide ion, the hydroperoxide anion, and oxygen radical, and the hydroxyl radical. Magnesium peroxide $MgO_2$ is a stable compound. In addition, the acetate ions may be further converted to the peroxyacetateion, which is stable at the pH of the slurry, at about 10.4. Impurity ions, such as $Fe^{2+}$ and $Fe^{3+}$ are removed from the slurry as particles for ferric oxide. The use of hydrogen peroxide or ozone supplements the intrinsic radicals developed during calcination and hydration. Ozone is added by sparging the slurry with ozonated air. Other adjuvants include a large number of established biocides, including all those listed in U.S. Pat. No. 6,827,766 B2 or nano-particles such as AgO and ZnO. Depending on the specific adjuvant and the amount added, the stability of the slurry may have to be re-established by the addition of dispersion agents. The use of adjuvants is not generally preferred because it may make the product toxic to humans, and increase the cost of production compared to the intrinsic biocide developed in the previous stages.

If required, impurities in the mineral such as sand, talc and magnetic particles are extracted during this process at any stage. The process to be used depends on the mineral source, whether macrocrystalline or cryptocrystalline, the impurities, the grinder and the grinder settings. Generally, for aquaculture applications, no such separation step is required.

Most importantly, it is noted that there is an expectation that there are no nanocrystalline particles present (i.e. with a diameter less than 0.1 microns) in the powder or slurry, and generally such particles are undesirable because, as fines, they are difficult to filter from the grinder air, and also to process in the steps described below, and to meet customer and community concerns about the toxicity of nanoparticles in general. The grinders are preferably grinding mills that entrains the ground particles in air, and which removes particles above about 0.5-1 micron before they can be further ground. This is a known art per se.

The intrinsic biocide for aquaculture produced using steps 1-5 described above produces either a powder or a 60% solids slurry of particles with a range of particle sizes from 0.1 microns to 100 microns as measured by a particle size analyser, and a Mg/Ca ratio in the range of 4-6.

The biocide activity of the intrinsic powder and slurry in aquaculture has been established in preliminary aquaculture trials on crayfish, prawns, salmon, tilapia, sea bass, silver perch, trout and milkfish.

The milkfish trials were conducted on fingerlings over 13 weeks in a 4 ha pond of 0.85 M L stocked with 250,00 fingerlings that are fed 3 times per day. The water is drained every 2 weeks. Weekly doses of 60 kg of the slurry were used. The pH was about 8.0-8.5. The odour of $H_2S$ was not present, compared to the control, and samples of the pond bottom were more solid, had less odour, and were lighter in colour. The fingerling mortality was 55% compared to 65% in the control, and the weight of the fingerlings was 34.9 g, compared to 22.4 g in the control. Thus the yield improvement was 84%. The fingerlings were transferred to sea pens (without further treatment), and at the harvest, the average fish weight was 7.3 kg, compared to 6.6 kg for the control. The quantity of premium fish, with the highest weight, increased by a factor of 4. The economic impact was estimated to be ten times higher than the cost of dosing.

The biocide activity of the intrinsic powder slurry for agriculture and other applications has also been established, and are the same as described by Sceats, and Sceats and Hodgson.

In one embodiment of the present invention, the nano-activity is demonstrated when brucite is used as a starting material. Brucite is the mineral of $Mg(OH)_2$ which is formed in a slow process where the grain size or crystallite size is in the region of microns and larger, and when ground, the particles exhibit no bioactivity. Brucite may be synthesised from sea water or brines by treating such with lime of hydrated lime to precipitate the Brucite. This brucite also exhibits no substantial bioactivity. When the brucite is flash calcined to give a very high surface area MgO, the MgO is formed as nano-scale crystallites within the particle, and hydration creates nano-scale $Mg(OH)_2$ within the particles. There is no observable change in the particle size, so that the process has transformed the structure of the brucite from macrocrystalline to nanocrystalline, and the defect density is accordingly very high, and the nano-activity is accordingly high.

The sprayed slurry of the hydrated nano-active $Mg(OH)_2$ has the effect of a disease preventative contact biocide, and is not a systemic biocide. The implication is that it has a broad spectrum response, typical of other biocides such as sulphur and copper compounds, and hydrogen peroxide, but without the toxic effects on all the biota on the leaf ecosystem. A n advantage of the nano-active particles is that the potentially adverse toxic impact of nano-particles on humans is mitigated because the particles cannot be breathed into the lung, and cannot diffuse through the skin into the human blood and lymph systems because the particles are too large. If ingested into the human gut, the particles are rapidly dissolved by the acids in the stomach. At high concentrations, the release of magnesium ions in the human or animal gut has the mild muscle relaxant effect of Milk of Magnesia.

In one embodiment of this invention, the materials described by Sceats and Hodgson are extended to include marine applications generally, in combination with other materials to form a setting material that, as a biocide, inhibits the formation of biofilms.

A first aspect of this invention may include the extension of the precursors that can be used for the production of the nano-active $Mg(OH)_2$ biocide described by Sceats and Hodgson, and the variation of the process conditions to achieve the biocidal properties. The prior art of Sceats and Hodgson claims a production process of carbonate minerals with the first step being grinding the precursor to produce a powder with a broad particle size distribution. The specification of the nano-active $Mg(OH)_2$ material was a particle size in the range of 0.5-100 microns. The feedstock for this prior art was generally magnesite, which is not abundant and is usually found with mineral impurities. In this invention, the range of preferred mineral precursors is increased from carbonatates such as magnesite $MgCO_3$ and dolomite $MgCO_3.CaCO_3$ to include brucite, $Mg(OH)_2$, where brucite include the mineral as well as synthetic magnesium hydroxide produced from brine, as a known art per se. Subsequent experiments have shown that magnesium hydroxide crystals made from brine itself are not nano-active because their surface area is too low. However, nano-activity can be induced by flash calcination of brucite to a nano-active MgO, followed by rehydration to form a nano-active $Mg(OH)_2$ material in the process described herein. The invention requires significantly different processing conditions that are disclosed herein. The synthetic brucite typically has a broad distribution of crystal sizes with a significant fraction above 100 microns, such that further grinding, wet or dry, is required to give a preferred distribution. The synthetic brucite material has been developed for ease of processing and for applications such as refractory manufacture in which the crystal size is generally as large as possible. For this invention, smaller crystal sizes are required, and the invention recognises that the synthetic process for brucite can be modified to yield a crystal size distribution that meets the requirements for this invention. Therefore, the first step in this modified process is one in which the size distribution may be achieved by either grinding or synthesising the precursors to give the desired particle size distribution. The first step can include grinding different fractions of the raw materials in a number of fractions to a number of different degrees of grinding and remixing the fractions to give the desired distribution, or including within a grinder segmentation of the materials to achieve the desired particle size distribution. The first step can include synthesising the precursor in a number of stages to give the desired distribution. For example, with synthetic brucite, boron can be used to control the crystallite distribution as described by Chisholm in U.S. Pat. No. 3,232,768.

A second aspect of the present invention may include the production of a nano-active product that can simultaneously provide bioactivity in the aqueous and the benthic ecosystems of an aquaculture pen or pond. In order to achieve a simultaneous impact, the product must be provided to both these ecosystems in doses that enable them to respectively impact on pathogenic species in each ecosystem. The general means of dosing used in aquaculture ponds is to deliver the product from a spray in a liquid form, or a metered spray of the liquid form or a powder form on the surface of the pond or pen. It has been found that the most advantageous distribution between ecosystems can be achieved by controlling the particle size distribution. It has been observed that very small particles, say below 10 microns in diameter have a very long residence time in the aqueous ecosystem. This is because their settling hydrodynamics is dominated by Brownian motion from the water, such that the settling velocity of such fine particles from the aqueous ecosystem is very low. This gives a prolonged residence time, so that the encounter of the particles with a pathogen is sufficiently probable that the bioactivity of the particles can exert themselves in this ecosystem. The fine nano-active particles can adhere onto the pathogen for direct bio-impact, or the cultured species or algae for indirect bio-impact. It has been observed that larger particles, say above 50 microns, have a shorter residence time in the aqueous environment because their hydrodynamics is dominated by gravitation, offset by turbulence of the water, such that they quickly fall into the benthic environment where they can exert their bio-impact. Intermediate sized particles have intermediate residence time. The most desired residence time depends on the location of the pathogen and the life-cycle of the pathogen. For example, some pathogens initially grow in benthic layer, before making an impact on the cultivated species. Therefore, the most effective means of controlling the residence time is to control the particle size distribution of the particles so that a sufficient fraction of the particles fall directly into the benthic ecosystem. Thus there is a preferred fraction of fines in the range of 0.4-10 microns that have a long residence time in the aqueous ecosystem, and course larger particles in the range of 50-100 microns that have a short residence time in that ecosystem, so that they act to improve the benthic ecosystem.

The specification of 0.5-100 microns was developed by Sceats and Hodgson to be such that the calcination process and the formation of a stable slurry could be readily achieved. For aquaculture, experiments have shown that the particle size distribution is preferably further specified to meet the residence time distribution of the particles in the aqueous ecosystem and the benthic ecosystem so as to have maximum bio-impact for the health of the cultivated species, as well as meeting the requirements for calcination and slurry stability. The preferred range of the particle size for aquaculture applications is within the 0.5-100 micron range claimed by Sceats and Hodgson, and is herein further specified for use in aquaculture. Thus key feature of this innovation is that the particle size distribution has become a parameter to optimise the biocidal impact of the nano-structured particles, rather than just a specification for the ease of calcination and stable slurry production. For example, for controlling the parasite vi brio in prawns, for an aquaculture pond that was 2 metres deep, the desirable particle size was such that at least 30% of the particles were less than 5 microns.

A third aspect of the invention is associated with the ingestion of the particles by the cultivated species. The prior art described by Sceats and Hodgson is focused on the use of nano-structured particles in agricultural crops, where the ingestion of the particles through the leaf stomata provides an additional benefit of enhancing the growth of the plant by the adsorption of magnesium for the production of chlorophyll. However, by analogy, the ingestion of the particles by the cultivated species in aquaculture provides a means of providing minerals for growth. The cultivated species have specific requirements for calcium for the growth of bones or shells, and the aqueous ecosystem may not be able to supply the required amounts. Further, calcium is also important in fish hatchery water supplies, because eggs tend to hydrate at low calcium concentrations and may not develop or hatch if the calcium concentration is too low. The cultivated species may ingest the calcium from the ions in the water (ie through the calcium hardness, which varies from lakes, rivers, estuaries and the sea) and from food, either directly or from algae that grow in the pond, or from additives such as calcium sulphate. The nano-active material is generally $Mg(OH)_2$ produced from hydration of MgO from calcining magnesite ores. Most magnesite ore, dominantly $MgCO_3$ contains some dolomite $MgCO_3.CaCO_3$. When the dolomite ore is processed, the product is a semi dolime $MgCO_3.CaCO_3$, and the formation of dolime MgO.CaO is suppressed at low calcination temperatures by the high partial pressure of $CO_2$. This process is described by Sceats and Horely (A U 2006904553), incorporated herein for reference. The dolomite crystallites are often found within the ground mineral feedstock particles along with magnesite and silica. Experiments have shown that the high porosity and surface area of the semi dolime produced in the flash calciner is such that the hydrated material, $Mg(OH)_2.CaCO_3$ exhibits a very fast acid decomposition which releases the calcium ions. In the gut of the fish, the acids in the stomach quickly release the calcium which can be ingested and can assist in the growth of the fish. It is preferable that the conditions of the calcination is such that the $CaCO_3$ is not calcined to lime. The absence of lime CaO, as dolime MgO.CaO, is such that the pH within the particle is maintained at about 10.4, and experiments have shown that the intake of the hydrated semidolime in the hydrated product has no adverse effects from stress that otherwise may have occurred had quicklime been formed. The desirable Mg/Ca balance in the product can be optimised to meet the requirements of the cultivated species, taking into account the calcium and magnesium in the water and in the food. Generally, the use of a mixture of Magnesite and dolomite as feed into the calciner can be varied so as to deliver the required Ca/Mg dose for growth of the cultivated species. More generally, mineral deposits of magnesite are found in layers, usually accompanied with dolomite layers, and the magnesite rich layers have some Dolomite as granular impurities and substitutional impurities. This benefit of specifying a Ca/Mg ratio is an important feature for aquaculture, but relatively unimportant for plants. Thus the specification for the production of the bioactive material by Sceats, and Sceats and Hodgson, failed to teach the benefits of controlling the input mineral to provide the desired bioactivity, and the desired Mg/Ca ratio in aquaculture applications to promote the health of the cultivated species, specifically with respect to the growth of bones and the hatching of eggs. This capability relies on the lack of toxicity of the nano-active species for ingested particle's because the acids in the stomach dissolve the particles and the released ROS is at sufficiently low doses that they are rapidly reduced in the digestive tract. The animal cells are capable of handling intense bursts of ROS because the release of ROS is a primary mechanism developed to combat infection. Thus nano-active particles have no toxicity to the cultivated species when ingested, and it is desirable that the calcium required for bones and shells is provided as $CaCO_3$, in particles with a high surface area so that ingestion is rapid. Thus calcined dolomite is preferable to the addition of ground limestone because the calcium is more accessible from semi dolime because of the higher surface area arising from calcination of the magnesium site.

A fourth aspect of the invention relates to the ability of the particles that are suspended for a short time to remove heavy metals, and excess phosphate and nitrogen, from the aquatic ecosystem. The specification provided by Sceats and Hodgson uses the surface area and porosity of the magnesium oxide as indicators of the nano-crystallinity of the powder, and therefore as indicators of the propensity of the particles to generate ROS at the nano-grain boundaries, and to retain these species as oxidants after hydration. However, experiments in aquaculture have revealed that the surface area of the magnesium hydroxide itself enables the controlled removal of heavy metals and phosphorous and nitrogen from the aquatic ecosystem during their passage to the floor of the pen. The accumulation of heavy metals, such as cadmium, copper, lead, chromium, arsenic, barium, cobalt, manganese and vanadium in the cultivated species may make the product unsuitable for human consumption. Very high concentrations of iron, from pyrites oxidation, are toxic to the fish. Magnesium hydroxide is well established as a product for removing iron and heavy metals from soils and water, where the metals precipitate to form insoluble hydroxides. Experiments have shown that the extraction efficiency is enhanced by the high porosity and surface area of the $Mg(OH)_2$ particles. Without being bound by theory, the reason for this is two-fold. Firstly, the reaction kinetics for the precipitation of insoluble hydroxides scales with the surface area of the Mg(OH)$_2$, and secondly, within the pores of the particle, the concentration of hydroxide ions is that of water saturated by the dissolution of Mg(OH)$_2$ at the pH of 10.4, rather than the pH of the water itself, which is preferably in the range of 7.0-7.6 for aquaculture. Thus the particles, falling through the water, efficiently extract the heavy metals from the aqueous ecosystem without the need for the particles to raise the pH to the levels required for heavy metal precipitation. These larger particles, having accumulated the metals, fall into the sludge of the benthic ecosystem. It is now current practice to extract the sludge from the pen after a number of days, and in this case, the heavy metals ions are removed from the pen. In the sludge, the larger particles sequester the heavy metals in the same way as Mg(OH)$_2$ is used to sequester heavy meals in soils, with a very low rate of leaching. It is preferable that there is a sufficient fraction of particles move through the aqueous ecosystem and fall into the benthic ecosystem to remove heavy metals from the aqueous system, and that there is a sufficient amount of such particles in the sludge, when removed, such that the heavy metals are extracted from the benthic ecosystem. Experiments have shown that the use of low surface area, low porosity Mg(OH)2 is not as efficient for heavy metal extraction. The invention is that the high porosity and surface area increases the yield of heavy metal ions that would be expected on the basis of the pH of the aqueous ecosystem.

In a similar manner, excess phosphorus, as the phosphate ion, and nitrogen as the ammonium ion, precipitate magnesium phosphate and magnesium ammonium phosphate in the particle pores at the pH of 10.4 and at a concentration of magnesium that is or order unity (directly from a surface site), and these materials are collected in the sludge. It is preferable that there is a sufficient fraction of particles move through the aqueous ecosystem and fall into the benthic ecosystem to remove excess phosphorous and nitrogen from the aqueous system, and that there is a sufficient amount of such particles in the sludge, when removed, such that the excess phosphorous nitrogen are extracted from the benthic ecosystem. It is noted that excess nitrogen is extracted when there is excess phosphate. In the case that the heavy metal ions are sufficiently low, the sludge is a useful plant fertilizer. Experiments have shown that the use of low surface area, low porosity Mg(OH)$_2$ is not as efficient for excess phosphorous and nitrogen extraction. The invention is that the high porosity and surface are increases the yield of excess phosphorus and nitrogen that would be expected on the basis of the pH and magnesium concentration in the aqueous ecosystem.

Therefore, in this innovation, the high surface area and porosity of the Mg(OH)$_2$ particles have been shown to control the extraction of heavy metal ions, phosphorous and nitrogen from the aqueous ecosystem, such that the cultivated species can grow healthily in a clean ecosystem, and the cultivated species can be consumed without adverse health impacts to humans.

A fifth aspect of the invention is associated with the capability of the Mg(OH)$_2$ particles to induce the flocculation of the particles in the aqueous phase. These particles may be suspended clays from soils following run off or disturbance, or organic matter such as faeces or uneaten food. In aquaculture practice, the optimum turbidity of the pond is dependent on the needs of the cultivated species, and generally it should not be too high to induce health problems, or too low to facilitate the capture by predators, such as birds. Magnesium hydroxide is an established flocculant because its high charge density causes the collapse of ionic boundary layers which others keeps the particles in suspension. Without being bound by theory, the Mg(OH)$_2$ particle have a point of zero charge at a pH of 10.4, and are thus negatively charged in an aqueous ecosystem with a pH in the ideal range of 7.5-7.0, whereas the particles that cause the turbidity and health problems have a point of zero charge below a pH of 7.0 and are charged positively. This is the basis of why Mg(OH)$_2$ is an excellent flocculant. However, the high surface area is such that the local response of these particles is fast, and the floc forms quickly through the charge neutralisation. Experiments have shown that the efficiency and rate of flocculation of a high porosity high surface area Mg(OH)$_2$ particle is larger than a comparable Mg(OH)$_2$ particles that have a lower surface area and lower porosity. Generally, this process removes the Mg(OH)$_2$ particles as well as the target particles, and they fall to the floor of the pen and are removed from the aqueous ecosystem. The larger particles trap a large number of smaller suspended particles that cause the turbidity. The flocculated particles are part of the sludge removed from the pens on a regular basis in many aquaculture practices.

It follows that the first and second aspects are optimised for small particles that have a long residence time, while the third and fourth aspects are optimised by larger particles that are sufficiently large that they pass through the aqueous ecosystems. The control of the particle size allows for such control.

The aspects considered above are concerned with the health of the aqueous ecosystem. Experiments have shown that the larger particles that move into the benthic ecosystem play a significant role in the health of that ecosystem, whether or not the particles have sequestered heavy metal ions or have deposited other particles. A sixth aspect is associated with the benefits of a healthy benthic ecosystem arising from the presence of nano-active Mg(OH)$_2$. It is often observed that the sludge at the base of an untreated aquaculture pen is septic, with a characteristic small of H$_2$S, it is acidic and anaerobic. This generally arises from the anaerobic bacterial decomposition of organic matter, from faeces and uneaten food, as a result of the high population density of the cultivated species. It is a known art that the dosing of sewage systems by Mg(OH)$_2$ is a means of raising the pH to a level that the decomposition is suppressed. Further, the use of nano-active Mg(OH)$_2$ may suppress the growth of pathogenic organisms in this benthic ecosystem, and mitigate their growth such that they do not significantly move into the aquatic ecosystem and infect the cultivated species. Experiments have shown that the sludge that is removed from the base of the pond or pen in which the nano-active Mg(OH)$_2$ has been added has very little sulphide smell, and is more compact compared to an untreated sludge. The degree of compaction is related to the same factors as flocculation, so that high surface area, and high porosity lead to more compact sludge. The practices in agriculture associated with sludge vary widely. In some cases, the sludge is decomposed in anaerobic digesters to produce a fuel, and experiments have shown that the presence of nano-active Mg(OH)$_2$ decreases the H$_2$S, and increases the methane content. In one practice, the sludge is sold as a fertilizer, and the absence of the H$_2$S odour is benefit. In another practice, the water is drained before being refilled and restocked, allowing a time for regeneration of the pond bed in aerobic conditions. The time for regeneration is significantly reduced if the anaerobic conditions of the sludge have previously been reduced and the sludge is compact, as a result of dosing with nano-active Mg(OH)$_2$.

A seventh aspect of the invention is the use of the nano-$Mg(OH)_2$ application in aquaculture is as a coating on aquaculture infrastructure. Experiments have shown the nano-active $Mg(OH)_2$ minimises the formation of biofilms. The result is that secondary growth of barnacles is also suppressed. Without being bound by theory, the mode of action of the nano-$Mg(OH)_2$ is believed to arise from the encapsulation of the particles by the extracellular extrusions of biofilm forming organisms, and the subsequent release of ROS and increase of the pH in the biofilms degrades the films, and leads to the disruption of the colonies of the biofilm forming organisms. This aspect is applicable to the maritime industry, as well as the aquaculture industry. For shipping, the presence of a biofilm causes a roughness on the hull, and the higher expenditure of energy. For aquaculture, the biofilm causes destruction of the pond enclosures, and fouling of equipment used to manage the cultivation. Depending on the application, the strength of the nano-Mg $(OH)_2$ coating can be enhanced by using additives. These include acrylic materials used in paints, and other stabilising materials. For example, the use of graphene fibres is particularly useful in such applications.

In this specification, the word 'comprising' is to be understood in its 'open' sense, that is, in the sense of 'including', and thus not limited to its 'closed' sense, that is the sense of 'consisting only of'. A corresponding meaning is to be attributed to the corresponding words 'comprise', 'comprised' and 'comprises' where they appear.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, with all changes which come within the meaning and range of equivalency therefore intended to be embraced therein. It will further be understood that any reference herein to known prior art does not, unless the contrary indication appears, constitute an admission that such prior art is commonly known by those skilled in the art to which the invention relates.

In one embodiment of the present invention, there is provided a reaction apparatus for producing biocide powder or a chemical detoxifier powder or a catalyst support from a carbonate mineral, comprising: a first grinder for carbonate compounds and a second grinder for hydroxide compounds; an externally heated counter flow flash calciner that produces high surface area oxides from the ground carbonate; an externally heated counter flow flash calciner that produces high surface area oxides from the ground carbonate; and a blender in which the calcined solid powders are mixed together, and or with other ground solids for the production of a biocide powder.

In another embodiment, the reaction apparatus further comprising a hydration reaction vessel for the production of the slurry product having an inlet for the blended powder and a water inlet; and a shearing apparatus for shearing the reaction mixture; and a steam outlet for release of steam from the reaction vessel, such that in use the reaction is controlled by allowing heat of hydration to raise the temperature of the reaction mixture, allowing water to boil off from the reaction mixture as hydration proceeds, and removing steam via the steam outlet to remove excess heat and control reaction temperature at boiling point and a means of quenching the slurry to below 60° C., preferably by transfer of the slurry to a cooled container and a means of cooling the slurry to ambient temperature; and a means of adding solid or liquid additives to the slurry.

In a further embodiment, the reaction apparatus is adapted for post-processing the bioactive power or slurry from the apparatus by one or more of the following steps:
  a sparging the powder or slurry with a gas adjuvant such as ozone to enhance bioactivity;
  adding and mixing liquid adjuvant compounds to the powder or slurry to enhance bioactivity;
  adding and mixing materials to the powder or slurry to make a biocidal coating product or
  adding and mixing materials to the powder or slurry to make a biocidal emulsion or foam.

In one embodiment of the present invention, there is provided a chemical composition as a powder adapted for use as a biocide, wherein the composition comprises: a powder of micron scale calcined particles which are formed from a mixture of carbonate compounds and hydroxide compounds, and which have additives to boost the biocide impact such as ozone, hydrogen peroxide wherein the particles have a porosity of greater than 0.5 and wherein the pore surface is largely composed of nano-crystalline structures.

The chemical composition as a slurry is adapted for use as a biocide, wherein the composition comprises a slurry produced by hydrating the powder of mentioned above with additives that stabilise the slurry.

In another embodiment, the chemical composition is presented as a coating material slurry adapted for use as a biocide, wherein the composition comprises a coating material produced by mixing the powder or the slurry mentioned above with additives that set the material when applied to a surface.

In another embodiment, the chemical composition is presented as a foam, spray or emulsion material slurry adapted for use as a biocide, biofilm inhibitor, or plant root repellant wherein the composition comprises a foam, spray or emulsion material produced by mixing the powder or the slurry mentioned above with additives that form a foam, spray or emulsion when processed.

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrial applicable.

The invention claimed is:

1. A chemical composition for use as a biocide comprising a powder of micron scale calcined particles comprising a mixture of
   a) at least one calcined carbonate compound containing oxygen defects selected from the group consisting of magnesite and dolomite, wherein the at least one calcined carbonate compound results from calcining at a temperature of about 750° C.;
   b) at least one calcined hydroxide compound selected from the group consisting of brucite and magnesium hydroxide, wherein the at least one calcined hydroxide compound results from calcining at a temperature that is about 450° C.; and
   (c) at least one component selected from the group consisting of ground limestone, lime, and hydrated lime,
   wherein the particle size distribution of the powder is 0.4-10 microns, the particles have a porosity of greater than 0.5 and wherein the pore surface is largely composed of nano-crystalline structures.

2. A chemical slurry composition for use as a biocide comprising the powder of claim 1 and further comprising carboxylic acid and at least one additive selected from the group consisting of hydrogen peroxide and ozone.

3. The chemical composition of claim 1, wherein the composition is applied as a coating material.

4. A chemical foam, spray, or emulsion composition for use as a biocide comprising the powder of claim 1 and further comprising oil.

5. The chemical slurry composition according to claim 2, wherein the carboxylic acid is acetic acid and the coating material sets when applied to a surface.

6. A chemical coating composition according to claim 3, further comprising acrylic material or graphene fibers.

7. A chemical slurry composition for use as a biocide comprising the powder of claim 1, wherein the carbonate compound is dolomite that has been processed to $MgO \cdot CaCO_3$.

8. The chemical powder composition according to claim 1 further comprising at least one additive selected from the group consisting of ozone and hydrogen peroxide.

* * * * *